United States Patent
Kabir et al.

(10) Patent No.: US 10,352,833 B2
(45) Date of Patent: Jul. 16, 2019

(54) MICROEXTRACTION CAPSULES AND METHOD OF MAKING

(71) Applicants: Abuzar Kabir, Dhaka (BD); Kenneth G. Furton, Homestead, FL (US)

(72) Inventors: Abuzar Kabir, Dhaka (BD); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 14/806,100

(22) Filed: Jul. 22, 2015

(65) Prior Publication Data

US 2017/0023452 A1    Jan. 26, 2017

(51) Int. Cl.
   *G01N 1/40*   (2006.01)
   *G01N 1/02*   (2006.01)
   *B01L 3/00*   (2006.01)

(52) U.S. Cl.
   CPC .............. *G01N 1/405* (2013.01); *B01L 3/508* (2013.01)

(58) Field of Classification Search
   CPC ... B01D 15/26; B01L 2400/043; B01L 3/508; B03C 1/00; G01N 30/00; G01N 2030/0073; G01N 2030/009; G01N 2030/0095; G01N 2446/00; G01N 2446/10; G01N 1/405
   See application file for complete search history.

(56) References Cited

U.S. PATENT DOCUMENTS

| | | | |
|---|---|---|---|
| 4,187,333 A * | 2/1980 | Rembaum | B01D 61/243 210/500.28 |
| 8,685,240 B2 * | 4/2014 | Malik | B01D 15/206 210/198.2 |
| 2006/0113231 A1 * | 6/2006 | Malik | B01J 20/103 210/198.2 |
| 2008/0287661 A1 * | 11/2008 | Jones | B01L 3/0275 530/418 |
| 2015/0094445 A1 * | 4/2015 | Bhuwania | B01D 53/228 528/210 |

OTHER PUBLICATIONS

Huang, X, Yuan, Dongxing; Preparation of stir bars for sorptive extraction based on monolithic material; Journal of Chromatography A, 1154, (2007), pp. 152-157.*
Shi et al; Determination of lignans in Wuweizi by using magnetic bar microextraction and HPLC; Journal of Separation Science; 36, (2013), pp. 3527-3533.*

* cited by examiner

*Primary Examiner* — Benjamin R Whatley
(74) *Attorney, Agent, or Firm* — Saliwanchik, Lloyd & Eisenschenk

(57) ABSTRACT

A microextraction capsule holding a sol-gel coating or monolithic bed with an affinity for one or more target analytes infused in a porous tube that can be placed in a sample matrix containing the target analytes. The microextraction capsule can include a magnetic wire to allow the capsule to be spun in the presence of the matrix to increase the rate of absorption of the target analytes. The microextraction capsule can be formed by infusing a sol solution into the porous tube and forming a metal oxide or hybrid inorganic-organic sorbent comprising gel from the sol within the pores of the porous tube or by forming a gel by sol-gel condensation with water followed by grinding the gel to a particulate gel and infusing the particles into a porous tube.

8 Claims, 2 Drawing Sheets

MICROEXTRACTION CAPSULES AND METHOD OF MAKING

BACKGROUND OF INVENTION

Sample preparation is an important but often neglected step in chemical analysis. The importance of an efficient sample preparation technique is even greater when dealing with trace and ultra-trace levels of target analyte(s) dispersed in complex sample matrices e.g., environmental, pharmaceutical, food, and biological samples. These samples are not generally suitable for direct injection into the analytical instrument for chemical analysis. This incompatibility is attributed to three main factors. First, the matrix ingredients may inflict a detrimental effect on the performance of the analytical instrument, or they may interfere with the analysis of target analytes. Second, the concentration of the target analyte(s) in the sample matrix may be too low to be detected by the analytical instrument. Third, the sample matrix may be incompatible with the analytical instrument. For example, aqueous solution containing the target analyte(s) cannot be injected into a gas chromatograph (GC) unless a solvent exchange (e.g., from water to an organic solvent) is carried out. As such, the primary objective of sample preparation is to isolate and concentrate the target analyte(s) from various sample matrices (biological, environmental, pharmaceutical, food etc.) into a new solvent/solvent system and to minimize matrix interference so that the cleaner analyte(s) solution can be introduced into the analytical instrument for separation, identification, and quantification without having a detrimental impact on the performance of the analytical instrument.

Classical sample preparation techniques such as liquid-liquid extraction (LLE) and solid phase extraction (SPE) are still among popular choices for environmental, pharmaceutical, toxicological, forensic and biological sample preparation. However, these procedures are time consuming, laborious, multi-step and utilize large volumes of toxic and hazardous organic solvents, leading to additional post-extraction steps such as solvent evaporation followed by sample reconstitution in a suitable solvent.

The solid-phase microextraction (SPME) is considered to be a new mode of sample preparation distinct with solvent-free/solvent-minimized microextraction, miniaturization, and automation. Due to the substantial advantages over conventional solvent-intensive sample preparation techniques, SPME has gained enormous popularity. However, SPME has a number of shortcomings. One major shortcoming of SPME (fiber format) is the miniscule amount (typically ~0.5 µL) of sorbent loading, which often results in poor extraction sensitivity. The low extraction sensitivity of fiber-SPME prompted the invention of a number of microextraction techniques with higher sorbent loading including in-tube SPME, Stir Bar Sorptive Extraction (SBSE), Micro Extraction by Packed Syringe (MEPS), rotating-disk sorptive extraction (RDSE), and thin film microextraction (TFME).

SPME and its different formats, modifications and implementations are generally governed by thermodynamic and kinetic criteria. Thermodynamic properties determine the maximum amount of analytes that can be extracted by a given mass of sorbent under a specific set of extraction conditions. Since higher volume of sorbent loading allows a higher amount of target analytes to be accumulated by the sorbent when adequate time is allowed to reach the extraction equilibrium, sorbent loading is directly related to extraction efficiency. Kinetics of the rate of extraction dictates the time required to reach the extraction equilibrium. The faster that extraction equilibrium is achieved, the higher the throughput in the analytical lab. As a result, there is a pressing demand to develop new microextraction techniques that can simultaneously satisfy the required sensitivity while permitting the shortest possible sample preparation time.

Critical evaluation of different microextraction systems reveals that shortcomings of all microextraction systems originate from: (1) coating technology used for immobilizing the sorbent on the substrate surface; and (2) the physical format of the extraction system that defines the primary contact surface area (PCSA) of the device where the extraction medium makes direct contact with the sample matrix containing the analytes. Therefore, if a sample preparation technique is to be highly sensitive as well as fast, both the coating technology and the primary contact surface area have to be augmented.

A majority of the shortcomings suffered due to the sorbent coatings used in commercially available microextraction technologies, such as, bleeding, washing away with organic solvent, long extraction equilibrium time, limited selectivity, extraction reproducibility, and swelling of the sorbent originate, primarily result from the process of immobilizing the organic polymer on the substrate surface. These coatings are generally created by physical deposition, followed by free-radical cross-linking reactions. The lack of chemical bonding between the polymer sorbent and the substrate is believed to be the primary cause of these coating-related problems. A number of alternative coating techniques have been proposed including: physical deposition; electrochemical deposition of conducting polymers; gluing with adhesives; and sol-gel column technology. Sol-gel column technology has proven to be the most convenient and versatile. In addition to the convenience of the coating process, sol-gel technology opens up the possibility of making multi-component materials that can be conveniently used to customize the surface morphology, selectivity, and affinity of the sorbent. The sorbent coating created by sol-gel technology is highly porous and is chemically bonded to the substrate. These coatings demonstrate remarkable thermal, solvent, and chemical stability. Due to its inherent porosity, a thin film of sol-gel coating can extend equivalent or higher sensitivity than commercially available, thick SPME coatings. The high porosity of the sol-gel coating also makes it possible to reach extraction equilibrium in a fraction of the time that is required by commercial SPME fibers.

Although tremendous efforts have been made to increase the sensitivity of the microextraction techniques by merely increasing the sorbent loading via expanding the surface area of the substrates, major challenge remains extracting target analytes directly from a complex sample matrix containing high volume of matrix interferents, such as, soil particulates, debris, biomasses, cells, proteins, fats, and tissues. These interferents may irreversibly adhere to the extraction sorbents of the device, leading to permanent damage and efficiency loss of the extraction device. Such samples require pretreatment, such as, filtration/centrifugation/protein precipitation or a combination thereof, to obtain a clean, particulate free, aqueous sample prior to extracting the analyte of extraction using SPE, LLE, SPME, SBSE, TFME and different modified techniques. Pretreatments including filtration and/or centrifugation involve the use of filter papers with sample transfer between one or more glass or plastic containers that results in moderate to significant analyte loss; depending on the physicochemical characteristic of the analyte and the type of filter paper/container used. Biological samples, e.g., blood, plasma, and urine, inevitably require protein precipitation to obtain a clean, particulate free environment prior to the extraction of the target analyte. Protein precipitation can result in significant analyte loss, especially if the analytes are medium polar or nonpolar analytes. Analyte losses during sample preparation pose serious legal, medical, and environmental ramifications when dealing with trace or ultra-trace levels of concentrations. Therefore, sample preparation should offer high analyte retention capacity, possess fast extraction kinetics, and should be capable of extracting a sample even when the environment sampled contains high volume of matrix interferents.

Sol-gel coatings chemically bind to many substrates, such as silica, when the gel is formed from the sol solution in the presence of the substrate. Because of the wide variety of possible sol components, a large number of sorbents for SPME are possible. Sol-gel monolithic beds are capable of achieving very high sample pre-concentration factors. Sol-gel technology has resulted in surface-bonded sorbent coatings on unbreakable fiber materials, e.g., Ni—Ti, stainless steel, titanium, and copper, and on substrates of different geometrical formats such as planar SPME (PSPME), and membrane SPME (MSPME). A wide variety of sol-gel silica, titania, zirconia, alumina, and germania-based precursors are commercially available. Additionally, a wide range of sol-gel reactive organic ligands are available to design hybrid organic-inorganic sol-gel coatings that can be used to target a particular analyte or sample matrix with improved selectivity, sensitivity, extraction phase stability and performance.

However, most microextraction devices are not designed for direct contact with the sample matrix when the matrix contains a high volume of particulates, debris or other matrix interferences that may cause irreversible damage to the sorbent coating. Hence, there remains a need for a simple device that can be placed in a sample matrix, easily retrieved, and capable of placing into an analytical device's sample introduction equipment for rapid sampling and reliable analysis of target analytes resident in a wide scope of environments.

BRIEF SUMMARY

Embodiments of the invention are directed to a microextraction capsule (MEC), where a porous tube has an absorbent gel within the pores of the tube. Optionally, a magnetic bar is attached to or resides within the porous tube. The microextraction capsule (MEC) can have a plastic tube, a glass tube, or an inert metal tube. The gel is a sol-gel formed gel comprising a metal oxide, such as silicon oxide, aluminum oxide, zirconium oxide, germanium oxide or titanium oxide. The gel can have alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof. The MEC can have the magnetic bar inserted in the length of the porous tube or coated by an inert plastic and attached to the porous tube.

A microextraction capsule (MEC) can be prepared by providing a porous tube, a sol comprising a metal oxide precursor, water, and optionally a solvent. The sol is contacted with the porous tube to infuse the sol within the pores. The metal oxide precursor and water condense to form a gel within the pores of the porous tube and in the confined spaces within the tube. Solvent, condensation byproduct, and any unreacted or fluid partially reacted sol components are removed, leaving the gel fixed within the pores and the confined spaces of the porous tube to form a microextraction capsule (MEC). The porous tube comprises a plastic tube, a glass tube, or an inert metal tube and the metal oxide precursor has the structure:

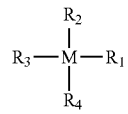

wherein, M is silicon, titanium, aluminum, zirconium, germanium, barium, gallium, indium, thallium, vanadium, cobalt, nickel, chromium, copper, iron, zinc, or boron, $R_1$, $R_2$, $R_3$ and $R_4$ are substituents groups, at least two of which are alkoxy, hydroxy, halide, or dialkylamino, and the remaining $R_1$, $R_2$, $R_3$ and $R_4$ independently comprise alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof.

Alternatively, a MEC can be prepared by condensing water and a sol into a gel from a metal oxide precursor, water, and optionally a solvent, grinding the gel into a multiplicity of particles, and infusing the particles into the porous tube, which can have one end sealed, and sealing any remaining open end of the porous tube. A magnetic wire can be incorporated into the MEC by attaching the magnetic wire to the external surface of the porous tube or inserting the magnetic wire into the porous tube.

DETAILED DISCLOSURE

An embodiment of the invention is directed to a microextraction capsule (MEC) device for sampling and sample preparation for biological, chemical, environmental, toxicological, or forensic sample analysis for trace and ultra-trace levels of organic analytes, and ionic analytes, including ions of metals. The device has a permeable tubular membrane that holds a monolithic sorbent bed created by the in situ formation or inclusion of preformed sorbent particles using sol-gel methods.

Figure 1:
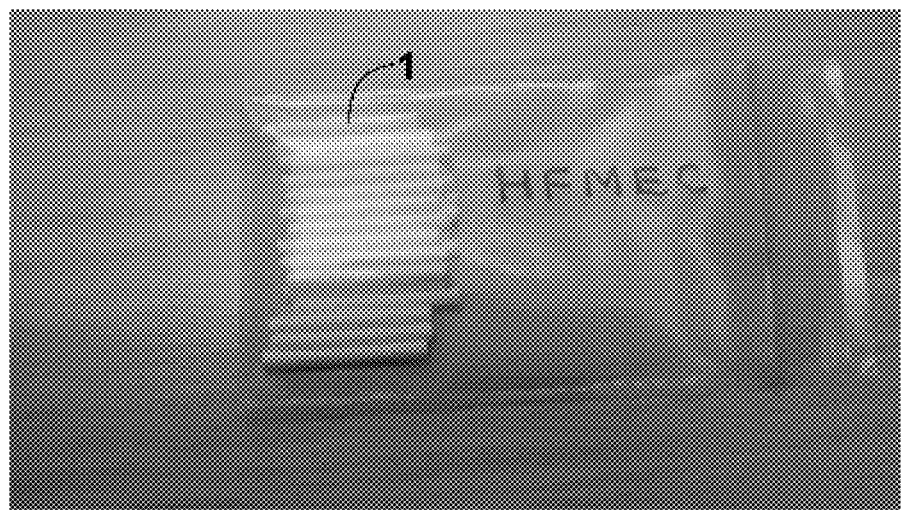
FIG. 1 shows a photograph of tubular porous membranes (1) used for the formation of microextraction capsules (MEC), according to an embodiment of the invention.

The MEC device sizes can be of various lengths, for example, but not limited to, 1 cm, 2 cm, 3 cm, 4 cm, or more, to permit extraction of very small to much larger sample sizes from biological fluids, environmental samples, industrial effluents, process samples, or any other sample type where at least one MEC is employed for extraction of one or more target analytes from the sample matrix. The permeable tubes (1), as shown in FIG. 1, can be polypropylene, polyethylene, nylon, Teflon®, or any other permeable plastic tube.

In an embodiment of the invention, a method for forming a microextraction capsule (MEC) involves the in situ formation of an internal monolithic sorbent bed; where an empty porous tubular membrane is contacted with a sol solution, wherein condensation of the sol components occurs within the pores to form a solid monolithic bed within the porous tube. Subsequent washing of the porous tube containing the monolithic sorbent with solvent, followed by drying under an inert atmosphere, removes trapped solvent and any non-gelled sol-components from the monolithic bed resulting in a MEC for sampling an analyte, according to an embodiment of the invention.

In another embodiment of the invention, preformed sorbent gel particles are formed from a bulk sol-gel condensation followed by fracturing the solid gel sorbent by grinding and screening to obtain a homogeneous particle size. The particles are mixed with solvent to form a slurry that is passed through the porous tubular membrane. Prior to passing the slurry into the tubular membrane, optionally, one end of the tubular membrane can be sealed if needed to retain the sorbent particles. After inclusion of the suspended particles from the slurry, open ends of the tube can be sealed to form a microextraction capsule. Sealing can be carried out thermally or with a resin.

Figure 2:
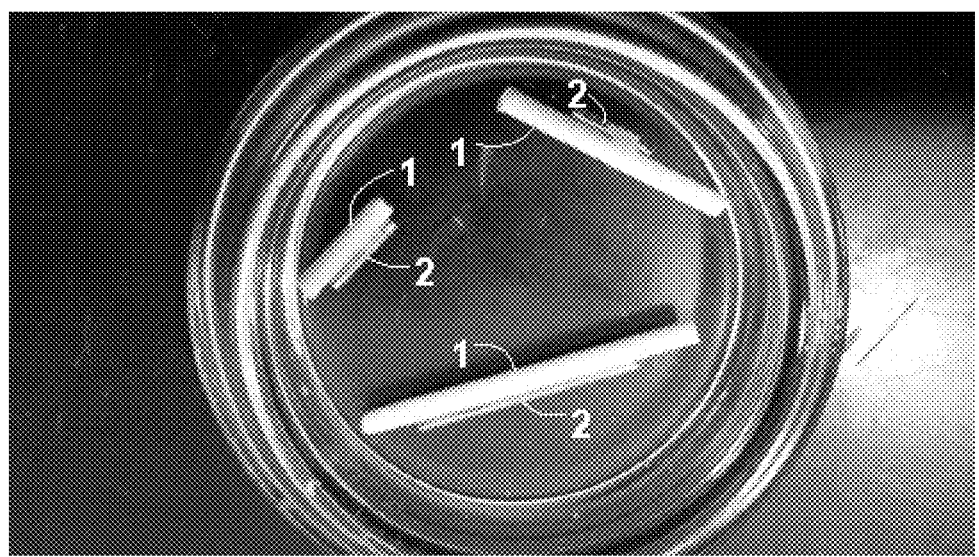
FIG. 2 shows a photograph of microextraction capsules having porous tubes (1) with integrated stirring bars, (2) externally attached or (2') internally attached, according to an embodiment of the invention.

In an embodiment of the invention, the microextraction capsule includes an attached magnetic wire (2) or (2') with the porous tube 1, as shown in FIG. 2, which can be coated with Teflon®, polypropylene, or any other inert polymeric coating such that the microextraction capsule can be magnetically spun in a solution to be sampled. Spinning the microextraction capsule enhances the mass transfer rate of an analyte between the sample solution and the microextraction capsule. A magnetic wire 2' can be inserted into the porous tube 1 rather than attaching it to the exterior of the capsule.

The elution, or back-extraction, of the extracted analytes from the microextraction capsule can be carried out by thermal desorption by exposing the MEC to the high temperature in a commercially available thermal desorption unit. From the thermal desorption unit, the analytes are purged into a GC inlet by a carrier gas flow. Alternatively, the analytes can be released by solvent desorption and elution where the MEC is exposed to a small volume of solvent to elute/back-extract the previously absorbed analyte in the MEC. The solvent can include a solute that has a high affinity for the analyte, such as, for example, a crown ether, cryptand, or other polydentate ligand for a metal ion. An aliquot of the analyte solution can be injected into the inlet of the analytical instrument for detection of one or more target analytes. The MEC device offers two significant advantages over conventional sample preparation techniques including: a high volume of microextraction sorbent that permits nearly exhaustive extraction even under equilibrium extraction conditions; and the micro porous tubular membrane protects the sorbent from matrix interferences from cell, proteins, lipids, biomasses, and soil particles. As a result, the MECs, according to an embodiment of the invention, allow a rapid and highly sensitive sample preparation from complicated environmental, biological, pharmaceutical, food, and forensic sites without requiring any sample pretreatment, including filtration, centrifugation, protein precipitation, or other steps prior to the extraction of at least one target analyte from these sites.

Figure 3:
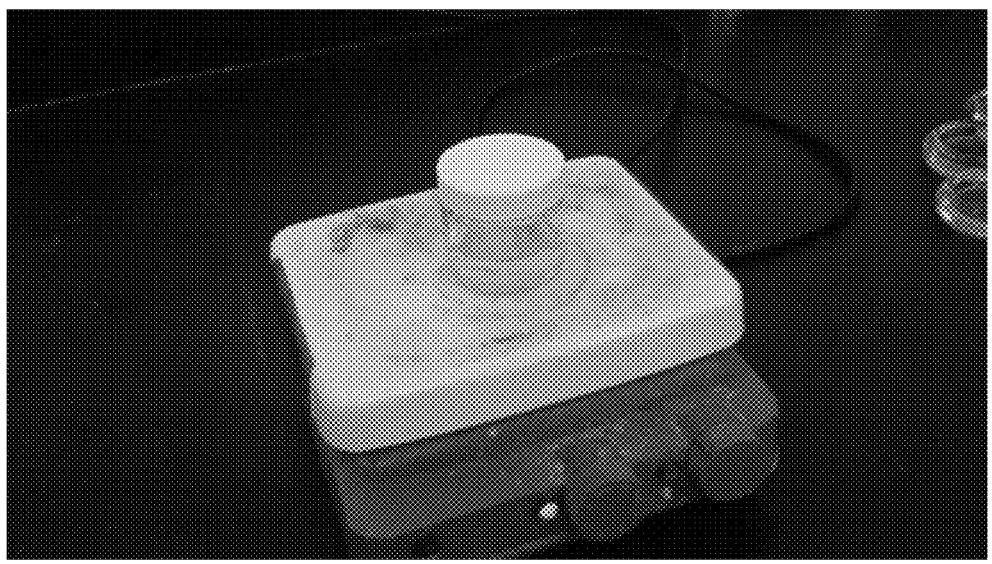
FIG. 3 shows a photograph of an analyte extraction using microextraction capsules (MEC), according to an embodiment of the invention.

The MEC device integrates sol-gel inorganic and/or hybrid organic-inorganic sorbents in the porous hollow tubular substrate. The porous substrate can be constructed from any natural or synthetic polymer, glass, or inert metal, wherein the pores are of micrometer dimensions, for example, but not limited to, about 0.5 to 100 µm. Furthermore, the MEC can include a magnetic stirring mechanism included in a single stand-alone unit. The device spins inside the matrix comprising a solution, when a container of the sample for analysis is placed on a magnetic stirrer, as shown in FIG. 3. In this manner the MEC permits a method that minimizes added solvent, and can be solvent-less, for the extraction of trace/ultra-trace level of organic analytes/ions/ heavy metals from different sample matrices.

In an embodiment of the invention, where the method for forming a microextraction capsule (MEC) involves the in situ formation of a monolithic sorbent bed, the sol solution is passed through the membrane to form a monolithic gel inside the tube. Trapped solvent and unreacted sol precursors can be removed by super critical $CO_2$ drying.

The sol that is absorbed in the polymer tubes can comprise precursors to gels that upon exposure to water from silica, titania, alumina, zirconia, germania, barium oxide, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or any combination thereof. Precursors of the gel of the monolithic sorption bed can have the general structure:

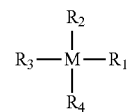

wherein, M is the precursor-forming element taken from any metal oxide, but not limited to, metal oxides listed above, $R_1$, $R_2$, $R_3$ and $R_4$ are substituents groups at least two of which are sol-gel active, wherein the sol-gel active groups include, but are not limited to, alkoxy, hydroxy, halides, and dialkylamino. Remaining R groups may be non-sol-gel active and may include alkyl moieties and their derivatives, arylene moieties and their derivatives, cyanoalkyl moieties and their derivatives, fluoroalkyl moieties and their derivatives, phenyl moieties and their derivatives, cyanophenyl moieties and their derivatives, biphenyl moieties and their derivatives, cyanobiphenyl moieties and their derivatives, dicyanobiphenyl moieties and their derivatives, cyclodextrin moieties and their derivatives, crown ether moieties and their derivatives, cryptand moieties and their derivatives, calixarene moieties and their derivatives, dendrimer moieties and their derivatives, graphene moieties and their derivatives, carbon nanotubes and their derivatives, chiral moieties and other similar non sol-gel active moieties.

A silica precursor can be any reactive silane compatible with any solvent of the sol and other components of the sol. For example, the silane can be a tetraalkoxysilane, tetraacetoxysilane, tetrachlorosilane, tetradialkylaminosilane or any other silica precursor. For example, tetramethoxysilane or tetraethoxysilane can be used as a silica precursor. In like manner, a tetraalkoxytitanate can be used as a titania precursor, trialkoxyaluminum can be used as an alumina precursor, and other metal alkoxides can be the source of zirconia, germania, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or barium oxide incorporated into the ultimate gel of the MEC. Generally, but not necessarily, the alkoxy and dialkylamino groups are $C_1$ to $C_4$ alkoxy and dialkylamino groups.

The sol can further comprise one or more siloxy precursors to the gel that reside as monoalkysiloxy, monoarylsiloxy, dialkylsiloxy, diarylsiloxy, or any combination of these precursors to a gel, where the alkyl or aryl groups can be unsubstituted, or substituted with functional groups for modification of the properties of the gel, to promote a specific affinity for one or more analytes, to react with other components included in the sol, and/or to have an affinity for a fabric surface. Hence, the siloxy precursor can be, but is not limited to, a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tridialkyaminoalkylsilane, tridialkyaminoarylsilane, didialkyaminodialkylsilane, dialkyaminoalkylarylsilane, didialkyaminodiarylsilane, or any combination thereof. The alkoxy and dialkylamino groups are generally, but not necessarily, $C_1$ to $C_4$ alkoxy and dialkylamino groups. The alkyl groups are generally, but not necessarily, $C_1$ to $C_4$ groups and aryl groups are generally, but not necessarily phenyl groups. The alkyl and/or phenyl groups can be substituted with a functional group, such as, but not limited to, amino, hydroxyl, carboxylic acid, acid anhydride, epoxy, acrylate, methacrylate, and vinyl. Functional groups in the gel formed within the tubes of the MECs can be hydroxy groups, acetoxy, hydrogen, chloro, dialkylamino, and γ-aminopropyl.

The sol can further comprise one or more organic precursors that have functionality that is reactive with the substituents, reactive intermediate substituents, or with the functionality on the siloxy precursors. The organic precursors can be monomeric, oligomeric, or polymeric, where there is at least one functionality on the organic precursor that can react with a reactive precursor substituent, a reactive intermediate substituent, or a reactive functionality of a siloxy precursor in the sol. When the organic precursor has a plurality of functionalities, the organic precursor can react with the functionality of another organic precursor in addition to reacting with a functionality of the sol or the gel that is not of the organic precursor. The organic precursor can have additional functionality for modifying the properties of the gel, functionality that provides an affinity for a target analyte, or functionality that provides an affinity for the surface of the porous tube of the MEC. The organic precursors, and functional groups on the siloxy precursors, can be reactive functionalities that do not involve hydrolysis and can be functionalities that undergo addition or polyaddition reactions rather than condensation reactions to be incorporated into the gel. In addition to hydroxy groups, the reactive groups can be complementary reactive functionalities to reactive groups of the siloxane precursors, and can be, but are not limited to, amino, hydroxyl, carboxylic acid, acid anhydride, epoxy, acrylate, methacrylate, and vinyl. Monomeric organic precursors include, but are not limited to, divinylbenzene.

Functionalities that provide specific affinity for analytes can include those which provide specific interactions, such as ionic functionalities, ion complexing functionalities, hydrogen bonding, plurally hydrogen bonding functionality, π-stacking functionality, or any other functionality that augments the van der Waals, dipole, induced dipole or other inherent intermolecular forces displayed between the gel and analyte. Functionalities that provide specific affinity for analytes include, but are not limited to, bidentate ligands, polydentate ligands, crown ethers, cryptands, aryenes, graphene, fullerenes, hydroxyfullerenes, and cyclodextrins. Functionalities that provide specific affinity for an analyte can be enantiomeric and not a racemic mixture for chiral selectivity of an analyte.

In another embodiment of the invention, preformed sorbent gel particles are formed from a bulk sol-gel condensation of the sol disclosed above, and water, followed by fracturing the solid gel sorbent by grinding and screening to obtain a homogeneous particle size that is chosen to be one capable of infusion into the pores of the porous tube used to form the MEC. The particles are mixed with solvent to form a slurry, which is passed through the porous tubular membrane. In embodiments of the invention, the particles can be functionalized nanoparticles that easily pack into the tube membranes, getting trapped inside the tubular membrane while the suspending solvent is vented from the tubes. Prior to passing the slurry into the tubular membrane, one end of the tubular membrane can be sealed to retain sorbent particles. After inclusion of the suspended particles from the slurry, the open end of the tube can be sealed to form a microextraction capsule. The porous tube can be sealed by melting the end of the tube or by applying a resin, such as an adhesive, for example, an epoxy resin, to the end of the tube.

It should be understood that the examples and embodiments described herein are for illustrative purposes only and that various modifications or changes in light thereof will be suggested to persons skilled in the art and are to be included within the spirit and purview of this application.

We claim:

1. A microextraction capsule (MEC), comprising an outer porous tube, an absorbent gel within pores of the porous tube, and a magnetic wire attached to or within the porous tube, where the porous tube is a plastic tube, a glass tube, or an inert metal tube and where the pore dimensions are 0.5 to 100 μm where the gel is a sol-gel formed gel comprising a metal oxide with alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof, and where the magnetic wire is inserted in the length of the porous tube or coated by an inert plastic and attached to the porous tube.

2. The microextraction capsule (MEC) according to claim 1, where the metal oxide is a silicon oxide, aluminum oxide, zirconium oxide, germanium oxide or titanium oxide.

3. The microextraction capsule (MEC) according to claim 1, where the porous tube is 1 to 4 cm in length.

4. A method of preparing the microextraction capsule (MEC) according to claim 1, comprising:
providing the porous tube;
providing a sol comprising a multiplicity of at least one metal oxide precursor, water, and optionally a solvent;
contacting the sol with the porous tube, where the porous tube is infused with the sol and where the metal oxide precursor and water condense to form a gel within pores of the porous tube and confined spaces within the tube; and
removing any solvent, condensation byproduct, or unreacted or fluid partially reacted sol components, where the gel is fixed within the pores of the porous tube and the confined spaces to form the microextraction capsule (MEC); and incorporating the magnetic wire, where incorporating comprises: attaching the magnetic wire to the external surface of the porous tube; or inserting the magnetic wire into the porous tube.

5. The method of preparing the microextraction capsule (MEC) according to claim 4, where the metal oxide precursor has the structure:

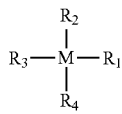

where, M is silicon, titanium, aluminum, zirconium, germanium, barium, gallium, indium, thallium, vanadium, cobalt, nickel, chromium, copper, iron, zinc, or boron, $R_1$, $R_2$, $R_3$ and $R_4$ are substituent groups, at least two of which are alkoxy, hydroxy, halide, or dialkylamino, and for at least one of the metal oxide precursors the remaining $R_1$, $R_2$, $R_3$ and $R_4$ independently comprise alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof.

6. A method of preparing the microextraction capsule (MEC) according to claim 1, comprising:

providing the porous tube;

providing a sol comprising a multiplicity of at least one metal oxide precursor, water, and optionally a solvent;

condensing the water and the sol to a gel;

grinding the gel into a multiplicity of particles;

optionally, sealing an end of the porous tube;

infusing at least a portion of the multiplicity of particles into the porous tube;

sealing any remaining open ends of the porous tube to form the microextraction capsule (MEC); and incorporating the magnetic wire, where incorporating comprises: attaching the magnetic wire to the external surface of the porous tube; or inserting the magnetic wire into the porous tube.

7. The method of preparing the microextraction capsule (MEC) according to claim 6, where the metal oxide precursor has the structure:

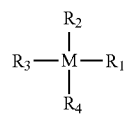

where, M is silicon, titanium, aluminum, zirconium, germanium, barium, gallium, indium, thallium, vanadium, cobalt, nickel, chromium, copper, iron, zinc, or boron, $R_1$, $R_2$, $R_3$ and $R_4$ are substituent groups, at least two of which are alkoxy, hydroxy, halide, or dialkylamino, and for at least one of metal oxide precursors the remaining $R_1$, $R_2$, $R_3$ and $R_4$ independently comprise alkyl moieties, arylene moieties, cyanoalkyl moieties, fluoroalkyl moieties, phenyl moieties, cyanophenyl moieties, biphenyl moieties, cyanobiphenyl moieties, dicyanobiphenyl, cyclodextrin moieties, crown ether moieties, cryptand moieties, calixarene moieties, or any derivative thereof.

8. The method of preparing the microextraction capsule (MEC) according to claim 6, where sealing comprises melting or fixing with a resin.

* * * * *